United States Patent [19]

Ngo et al.

[11] Patent Number: 4,977,077
[45] Date of Patent: Dec. 11, 1990

[54] INTEGRATED SOLID-PHASE IMMUNOASSAY

[75] Inventors: That T. Ngo; Raphael C. Wong, both of Irvine, Calif.

[73] Assignee: Bioprobe International, Tustin, Calif.

[21] Appl. No.: 185,218

[22] Filed: Apr. 25, 1988

Related U.S. Application Data

[63] Continuation-in-part of Ser. No. 664,444, Oct. 24, 1984.

[51] Int. Cl.$^5$ .............................................. C12Q 1/00
[52] U.S. Cl. ........................................ 435/7; 436/501;
 436/537; 436/547; 436/800; 436/822; 436/518
[58] Field of Search .................... 435/7; 436/501, 537,
 436/547, 800, 822, 518; 536/81

[56] References Cited

U.S. PATENT DOCUMENTS 4,680,275 7/1987 Wagner ............................ 436/518

Primary Examiner—Amelia Burgess Yarbrough
Assistant Examiner—Mindy B. Fleisher
Attorney, Agent, or Firm—Nilsson, Robbins Dalgarn, Berliner Carson & Wurst

[57] ABSTRACT

The presence of an antigenic analyte ligand in a liquid sample is determined by (1) mixing the sample with a fluorescently labeled ligand immunologically complexed onto a solid phase supported antibody capable of exchanging the fluorescently labeled ligand with the analyte ligand in the sample and (2) measuring the fluorescence of the resulting liquid phase without measuring the fluorescence of the resulting solid phase and without separating the resulting solid phase from the resulting liquid phase.

4 Claims, 1 Drawing Sheet

INTEGRATED SOLID-PHASE IMMUNOASSAY

This is a continuation-in-part of Ser. No. 664,444, filed Oct. 24, 1984.

FIELD OF THE INVENTION

This invention relates generally to the field of clinical biochemistry and, more particularly, to methods for determining the presence and quantity of immunological compounds.

BACKGROUND AND SUMMARY OF THE INVENTION

There is a continuing need for a facile and accurate determination of the presence and quantity of biologically-active substances which may be present in fluids at extremely low concentrations. For example, it may be important to determine the presence of exogenous drugs in body fluids, or the presence of various endogenous substances which may be of diagnostic significance. Traditional methods of qualitative and quantitative analysis have been insufficient due to the fact that such substances are present in extremely small amounts, and because small differences in concentration are often of substantial significance.

For example, aminoglycoside antibiotics exhibit high potency and a broad-spectrum anti-bacterial activity against gram-negative and gram-positive organisms. However, these antbiotics have a narrow therapeutic index and are potentially nephrotoxic. The risk of nephrotoxicity is greater in patients with impaired renal function and in those who receive high dosage or prolonged therapy. Consequently, patients treated with aminoglycosides should be under close clinical observation and serum concentrations of aminoglycosides should be monitored to assure adequate levels and to avoid potentially toxic effects. For example, tobramycin treatment of gram-negative infection requires peak serum concentrations of at least 4 mg/L, and concentrations exceeding 10 mg/L are associated with nephrotoxic side effects.

Immunological binding assay methods have undergone evolution from the original competitive binding radioimmunoassay in which a specific radio-isotope-labeled antigen is made to compete with the analyte (antigen) from the test sample for binding to a specific antibody. Generally, the analyte is quantitated by measuring the proportion of radioactivity which becomes associated with the antibody (through attachment of the labeled antigen thereto) to the radioactivity that remains unassociated with the antibody after having physically separated the antibody-bound antigen from the test sample. This proportion is then compared to a standard curve.

Radioimmunoassay techniques are inherently selective, and have enabled the determination of substances which are present in body fluids in amounts as low as $10^{-12}$ to $10^{-15}$ molar. However, the use, production, shipping, handling, and disposal of radioactive material and the maintenance of the required counting equipment has presented substantial disadvantages to its use.

The use of fluorescence labels, attached to either the antibody or the competing ligand, that is, antigen or hapten, offers significant advantages over radioimmunoassay procedures. Such fluorescence assays are based o the assumption that the antibody is unable to distinguish between the labeled substance (antigen) and the unlabeled analyte. Quantitative analysis of the analyte may be accomplished by determining the change in the fluorescence properties of the labeled antigen upon binding to the antibody. If this change in the fluorescence of the bound labeled ligand is sufficiently different from the unbound labeled analyte ligand, it may be used to quantitate the analyte concentration without the separation of the bound labeled antigen from the labeled unbound antigen in the test solution. These assays, based on changes in fluorescence properties upon binding, have employed fluorescence properties such as excitation transfer, polarization, enhancement and quenching.

Due to the fact that separation is not required, these assays have been termed homogeneous assays and examples of this technique are well known in the art. For example, in *Analytical Biochemistry*, 108 (1980) 156–161, a fluorescein dye pair is employed in a fluorescence excitation transfer immunoassay for morphine. *Journal of Immunological Methods*, 42, (1981) 93–103 describes a homogeneous substrate-labeled fluorescent immunoassay for IgG in human serum. *Clinica Chimica Acta*, 73 (1976) 51–55 and *J. Clin. Path.*, 30 (1977) 526–531 describe, respectively, homogeneous polarization and quenching fluoroimmunoassays for the determination of gentamicin levels in body fluids. Further, *Clinical Chemistry*, Vol. 27, No. 7 (1981) 1190–1197, describes a homogeneous fluorescence polarization immunoassay for monitoring aminoglycoside antibiotics in serum and plasma.

Major limitations of homogeneous fluoroimmunoassays are (1) the presence, in body fluids, of endogenous interferences which generally result from the inherently small signal from the analyte in the presence of a high background emission from endogenous proteins and other species; (2) the generally lower sensitivity limit; and (3) the greater number of liquid transferring steps (pipetting).

Accordingly, non-homogeneous or heterogeneous fluorescence immunoassays are accomplished by the separation of the antibody-bound labeled ligand complex from fluorescing or other substances present in the solution by chemical, physical or immunological differences between the analyte ligand and the antibody-ligand complex. For example, the antibodies may be absorbed or bonded covalently to paper disks, glass or plastic beads or other solid supporting material. When the antibodies are immobilized on the solid support, labeled ligands and the analyte ligand are introduced and allowed to compete for available binding sites on the antibody. The bound labeled fraction is then separated from the labeled ligand and unlabeled ligand remaining in the solution by washing away the unbound labeled and unlabeled ligands from the complex. The labeled ligand-antibody complex can then be measured directly, without removal from the solid phase, by a modified fluorometer, or the fluorescently-labeled ligand can be removed from the solid phase by washing with an appropriate denaturant and measured in the resulting solution in a fluorometer. Alternatively, a ligand attached to a solid support may compete with the analyte ligand for binding with a labeled antibody. The labeled antibody may then be measured after separation and washing to remove the unbound, labeled antibody.

In *Clinical Chemistry*, Vol. 25, No. 9 (1979), Curry et al. describe a competitive binding fluorescence immunoassay wherein antigen labeled with a fluorescent dye competes with analyte for a limited amount of antibody immobilized on polyacrylamide beads. *Clinica Chimica Acta*, 78 (1977) 277–284 describes a non-competitive method for the determination of human serum components based upon the fluorescence of a solid phase antibody. *Clinica Chimica Acta*, 102 (1980) 169–177 details the use of a solid-phase fluorescently-labeled antibody for measurement of serum immunoglobulins. A double antibody fluorescence immunoassay for tobramycin which employs fluorescein-labeled tobramycin, separation and resuspension is described in *Clinical Chemistry*, Vol. 27, No. 2 (1981) 249–252.

Additional references which describe fluorescence immunoassays are: *Clinical Chemistry*, Vol. 25, No. 3 (1979) 353–361; *Journal of Pharmaceutical Sciences*, Vol. 70, No. 5 (1981) 469–475; O'Donnell et al., *Analytical Chemistry*, Vol 51, p. 33A (1979); and Nakamura et al., *Immunoassays in the Clinical laboratory:* 211–226 (1979).

While heterogeneous assays have provided advantages over the homogeneous technique due to the separation of the solid-phase antibody-antigen complex, these advantages are ameliorated by the requirement of additional steps in the assay procedure which are not only labor-intensive, but provide an increased possibility of experimental error.

Accordingly, it has been a desideratum to provide a fluoroimmunoassay which would combine the integrated procedure of the separation-free nature of the homogeneous assay with the superior signal-to-noise ratio of the non-homogeneous assay, that is, to conduct a heterogeneous fluoroimmunoassay without the necessity of the separation of the antibody-bound ligands from unbound ligands.

According to the present invention, the presence of an analyte ligand in a liquid phase is determined by fluorescence immunoassay by providing a solid phase supported antibody complexed with fluorescently labeled ligand to a liquid containing the analyte ligand or by providing a solid phase supported antibody and sequentially contacting the solid phase supported antibody first with the analyte ligand and then with the fluorescently labeled ligand, and measuring directly and with great advantage, the fluorometric activity of the fluorescently labeled ligand in the liquid phase without carrying out any separation of the fluorescently labeled ligand bound to the solid phase supported antibody complex.

For example, in one embodiment of the invention, upon mixing fluorescently labeled ligand complexed to solid phase antibody with analyte ligand solution, the analyte ligand undergoes exchange with the solid phase antibody-fluorescently labeled ligand complex, that is, the analyte ligand displaces the fluorescently labeled ligand out of the solid phase antibody-fluorescently labeled ligand complex.

More particularly, in a preferred embodiment, the present invention consists in mixing a solid phase supported antibody-fluorescently labeled antigenic analyte ligand complex with a liquid phase sample containing the antigenic analyte ligand to be determined, the liquid phase sample initially containing no fluorescently labeled antigenic analyte ligand, where the unlabeled antigenic analyte ligand in the liquid phase sample displaces a part of the fluorescently labeled antigenic analyte ligand from the solid phase supported antibody-fluorescently labeled antigenic analyte ligand complex into the liquid phase, resulting in (1) a solid phase containing:

(a) solid phase supported antibody fluorescently labeled antigenic analyte ligand, and
(b) solid phase supported antibody-unlabeled antigenic analyte ligand complex, and (2) a liquid phase containing:

(a) fluorescently labeled antigenic analyte ligand displaced from the solid phase supported antibody-fluorescently labeled antigenic analyte ligand complex, and
(b) a reduced concentration of unlabeled antigenic analyte ligand;

measuring the fluorescence of the resulting liquid phase without measuring the fluorescence of the resulting solid phase and without separating the resulting solid phase from the resulting liquid phase; and determining the concentration of the antigenic analyte ligand in the sample corresponding to the measured fluorescence of the resulting liquid phase.

In another embodiment, a highly purified antibody capable of immunologically binding with the analyte ligand is attached to a solid material and mixed with the analyte ligand and a fluorescently-labeled ligand which is capable of binding to the antibody. The fluorescently-labeled ligand and the analyte ligand, if any, are allowed to compete for immunological binding to the antibody attached to the solid material, and the presence of the analyte ligand is assayed by determining the fluorescent activity in the liquid phase without separating any of the bound fluorescent antigen from the solid material.

In another embodiment, the method can be conducted by providing solid-phase supported antibody to a liquid containing analyte ligand to allow analyte ligands to occupy some of the antibody binding sites. Subsequently, a known and fixed amount of fluorescently labeled ligand is introduced to occupy the remaining unoccupied antibody binding sites. The fluorometric activity of the remaining (unbound) fluorescently-labeled ligand is directly and advantageously measured in the liquid phase without separating any of the bound fluorescently labeled ligand from the solid-phase supported antibody.

In another embodiment, the method may be conducted by providing a fluorescently-labeled purified antibody and a ligand attached to a solid material which is capable of immunologically binding with the fluorescently labeled antibody. The solid material supporting the ligand is mixed with the labeled antibody and the analyte, and the solid phase labeled ligand and the analyte are allowed to compete for immunological binding to the antibody. The presence of the analyte ligand is then determined by determining the fluorescent activity of the fluorescently labeled antibody directly in the liquid phase without separating any of the bound fluorescent antibody from the solid material.

While the invention will be exemplified by reference to specific assays for aminoglycoside antibiotics, the invention in general and certain aspects in particular are broad in scope. In general, the invention provides a sensitive method for determining the presence and quantity of a wide range of analytes by measuring the fluorescent activity of fluorescently-labeled ligands. Measurement is made directly in a liquid phase above a solid phase constituted of bound, labeled ligand-antibody complexes without separating the liquid phase from the solid phase. The specific examples hereinafter described regarding the determination of gentamicin and tobramycin are selected to exemplify the invention, which is applicable to the determination of the presence and quantity of any substance which may be assayed by immunological techniques.

DESCRIPTION OF THE PREFERRED EMBODIMENTS

Figure 1:
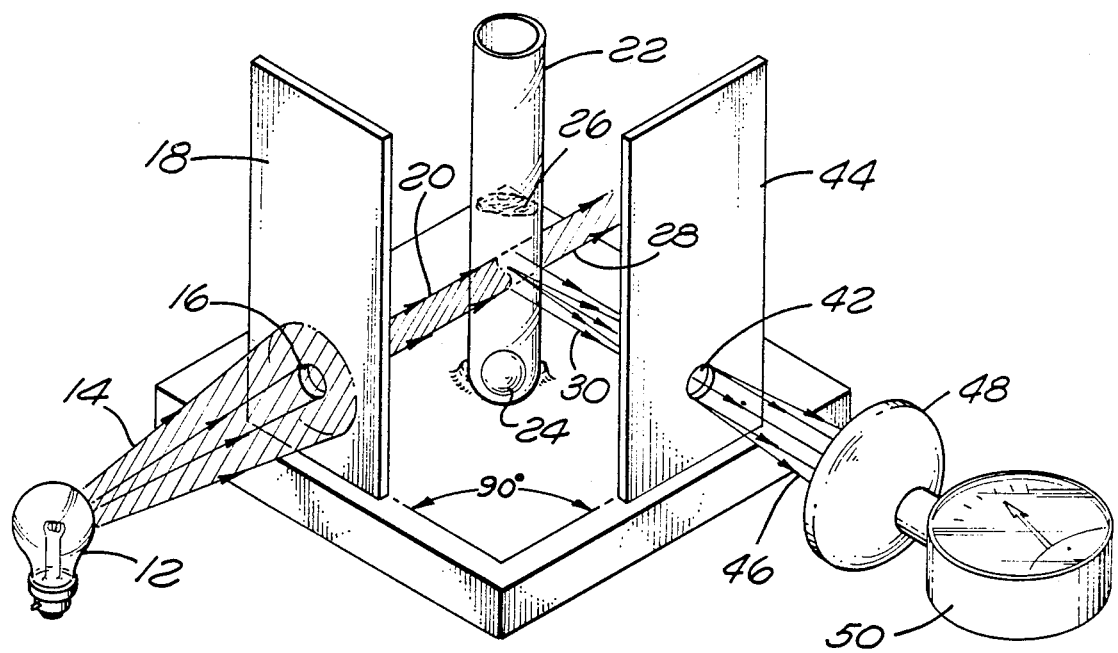
FIG. 1 is a diagrammatic perspective view of a system for carrying out the fluorometric measurements of the present invention.
Figure 2:
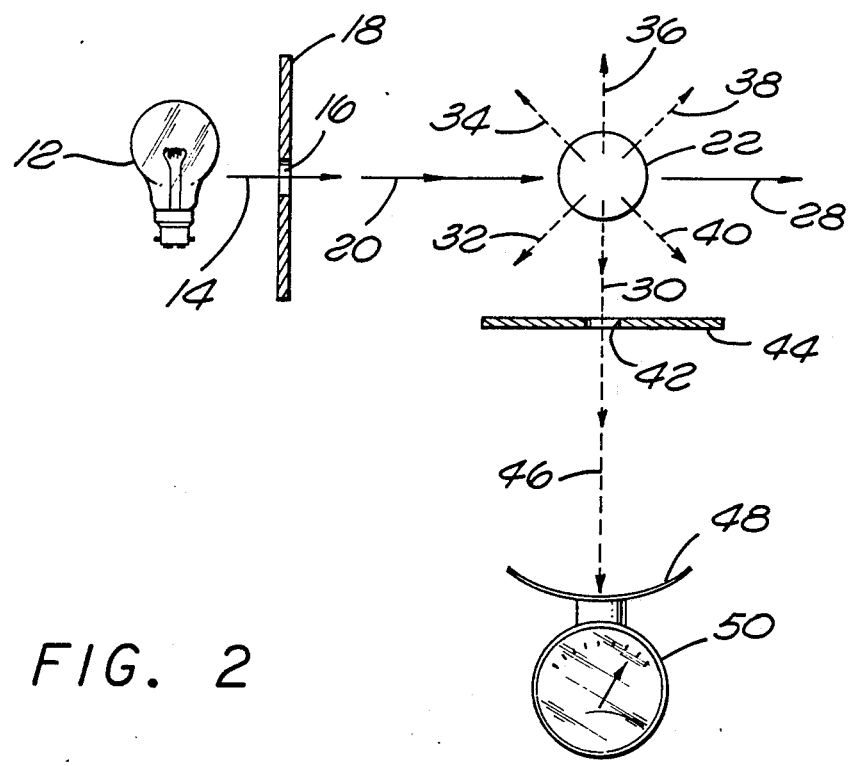
FIG. 2 is a diagrammatic plan view of elements of such system.

Referring to FIG. 1 of the drawing, a light source 12 produces a beam of light 14 which is focused by means of an aperture 16 in a shield 18 into a focused light beam 20. Light beam 20 impinges upon a test tube 22 containing a bead 24 in a solution 26. Fluorescent materials present in solution 26 above ball 24 are thereby caused to fluoresce. Fluorescent light beam 28 exits test tube 22 in the direction of propagation of focused light beam 20. Fluorescent light beam 30 exits test tube 22 in a direction 90° to the direction of propagation of focused light beam 20. Other fluorescent light beams 32, 34, 36, 38 and 40 shown in FIG. 2 exit test tube 22 at various angles to the direction of propagation of focused light beam 20. Fluorescent light beam 30 passes through an aperture 42 in a shield 44. Fluorescent light beam 46 emerging from aperture 42 is focused by a lens 48 upon a detector 50.

Measurement of the fluorescence of the liquid phase without measuring the fluorescence of the solid phase and without separating the solid phase from the liquid phase is made by focusing the excitation light beam of a fluorometer on the solution above the solid phase without permitting any of the excitation light to impinge on the solid phase, as shown in FIG. 1. Such focusing may be accomplished by means of lenses, filters, shutters or shields. Since any fluorescently labeled ligand present in the liquid phase will fluoresce upon excitation by a light beam and fluorescent light will be emitted in all directions, a detector positioned 90° to the direction of the excitation light beam will measure the intensity of the emitted fluorescent light with minimum interference from the excitation light beam. The fluorescent intensity is directly proportional to the concentration of fluorescently labeled ligand in the solution above the solid phase, which in turn, is proportional to the concentration of the ligand in the sample.

The invention is applicable to hapten, antigen and antibody assays, and to competitive, non-competitive and exchange variations thereof. For example, an unlabeled antibody may be linked to the solid phase for use with a labeled ligand or an unlabeled ligand may be linked to the solid phase for use with a labeled antibody. The analyte ligand and labeled ligand may be added to the solid phase supported antibody, for example, sequentially, in a non-competitive system, or simultaneously as a competitive system or the solid-phase supported antibody with its complexed fluorescently labeled ligand may be added to analyte ligand solution in an exchange system.

A wide variety of solid-phase support material for heterogeneous fluoroimmunoassays is known in the art and may be employed in the assay of the present invention. For example, paper discs, small glass or plastic beads or Sephadex particles may be employed. Generally, polyamide (Nylon) or polystyrene beads are preferred and beads having a diameter of from ⅛ to ¼ inch in diameter are particularly preferred, for ease of handling.

The fluorescence label should possess stability, have high absorptivity and fluorescence, and fluoresce at appropriate wavelengths. Such labels include fluorescein, phycobiliprotein, tetramethylrhodamine, umbelliferone, isoluminol, and nicotinamide derivatives. The preferred fluorescence label for any particular assay is selected by the requirement that the fluorescence label not interfere with the antibody-ligand binding. With respect to the aminoglycoside drugs hereinafter described, the preferred fluorescence label is fluorescein isothiocyanate. Procedures for the preparation of fluorescently-labeled antibodies and ligands are known in the art and constitute no part of the invention described herein. Similarly, methods for the binding of antibodies and ligands to solid support material are also well known.

In order to allow the direct determination of the fluorescent activity in a liquid phase without separating bound fluorescent antibody complexes from the solid material, it is important that the antibodies employed be substantially more pure than those heretofore used in heterogeneous fluoroimmunoassays. Methods for the purification of antibodies are described in *Immuno Chemistry in Practice,* Blackwell Scientific Publications (1982), which is incorporated herein by reference. Particularly, antibodies may be purified by salt fractionation. DEAE chromatography may also be used. The preferred method for antibody purification, however, is immunoaffinity purification, wherein insolubilized ligands bind specifically to the corresponding antibodies. The purified antibodies are then eluted from the column.

EXAMPLES

Purification of Anti-Aminoglycoside Antibodies

A 0.5cm × 20cm column of Sepharose Cl-4B containing bound aminoglycoside, was equilibrated with phosphate-buffered saline solution. Thereafter, 1ml of rabbit antiaminoglycoside serum was passed through the column. The column was washed with phosphate-buffered saline until the absorbence of the eluate at 280 nm was less than 0.02, showing that no protein was coming through the column. The column was then eluted with 0.1 M glycine-HCl, pH 2.5, containing 10% tetrahydrofuran. Pure antiaminoglycoside antibodies were desorbed from the column when the pH of the eluate became acidic (pH 2.5).

Synthesis and Purification of Fluorescein-Labeled Aminoglycosides

The labeled gentamicin and tobramycin hereinafter employed were prepared by dissolving 2mg of the aminoglycoside in 1ml 0.05 M $Na_2CO_3$ (pH 9.0), and adding 1 mg of fluorescein isothiocyanate. This reaction was allowed to proceed at room temperature in the dark for two hours, and the solution was acidified to pH 2 to 3 with concentrated hydrochloric acid. This acidified solution was extracted five times with 5ml ethyl acetate and five times with 5ml hexane. The aqueous solution was neutralized to pH 8-9 with 1 N NaOH and applied to a 1 × 50cm column of Sephadex G-15 which had been equilibrated with 0.05 N $Na_2CO_3$ (pH 9). The column was eluted with the same buffer. Fractions of 15ml were collected and monitored for both fluorescein and aminoglycoside activities.

PREPARATION OF SOLID PHASE MATERIAL PREPARATION OF ANTIBODY COATED BEADS

Polystyrene beads of ¼ inch diameter were washed two times with ethyl alcohol, followed by five times with distilled water. The beads were then air-dried.

A quantity of 2.5ml of glutaraldehyde solution (25%) was added to 2.5ml of sodium carbonate solution (0.1 M, pH 11.7), resulting in a 12.5% glutaraldehyde solution. After ten minutes at room temperature the solution was poured into 60 ml of sodium phosphate buffer (0.1 M, pH 7.0) in a tissue culture flask. Then 250 prewashed polystyrene beads were added and left at room temperature for twelve hours, followed by washing three times with 60ml of sodium phosphate buffer. The beads were then drained and transferred to a second culture flask containing 0.22mg of purified antibody in 60ml of sodium carbonate buffer (0.1 M, pH 9.6). The beads were then incubated with the antibody solution for three days at 4.C. After incubation, the beads were washed three times with 60ml of phosphate buffered saline (0.01 M sodium phosphate buffer, pH 7.4, 0.15 M sodium chloride) containing 0.1% bovine serum albumin.

It should be noted that the concentration of the purified gentamicin or tobramycin antibody can be increased or decreased in the culture flask, dependent upon the concentration of the analyte to be determined. For example, if the analyte is present in high concentrations, the amount of antibody on the beads should be increased.

Preparation of Fluorescent Conjugate Coated Antibody Beads

Three hundred polystyrene beads were first rinsed once with 200 ml ethyl alcohol and three times with 2 liters each of distilled water. The beads were then immersed in 300 ml 12.5% glutaraldehyde in 0.1 M potassium borate buffer at pH 8.5 and shaken gently for 24 hours at room temperature. Following the removal of the glutaraldehyde solution, the beads were rinsed four times with 2 liters each of distilled water and 2 times with 2 liters of 0.1 M sodium bicarbonate solution at 30 minute intervals. The beads were then immersed in 300 ml of affinity purified anti-drug antibody in 0.1 M sodium carbonate buffer at pH 9.6 and shaken gently for 24 hours at room temperature. The concentrations of antibody were 15 to 38 $\mu$g/ml. The beads were then successively rinsed twice in 2 liters of phosphate buffered saline, once in 0.35 M sodium chloride in phosphate buffered saline and again in phosphate buffered saline. After these rinsings the beads were placed in 300 ml of phosphate buffered saline containing 1.5 ml of 10 $\mu$mole/ml fluorescein drug conjugate for 24 hours at room temperature. Then the beads were rinsed in 2 liters of, respectively, phosphate buffered saline, 0.35% sodium chloride in phosphate buffered saline, diluted phosphate buffered saline (1:20 phosphate buffered saline and distilled water), and phosphate buffered saline. After these rinsings, the beads were stored in phosphate buffered saline and were ready for use. When not in use, the fluorescent conjugate coated beads were stored at 4° C.

Assays

A wide variety of known techniques and fluorometers may be employed in carrying out the assay of the present invention. However, in the assays hereinafter described, a Sequoia-Turner Model 450 Fluorometer is employed. All assay steps may be conducted at room temperature.

EXAMPLE 1

Fifty microliters of serum sample or serum based standard was first diluted with 1.3 ml of phosphate buffered saline. Then fifty microliters of the diluted serum was added to a 12 x 75 mm glass test tube containing 1.3 ml phosphate buffered saline. A fluorescent conjugate coated antibody bead was added by simply dropping the bead into the tube. Alternatively, the bead was first placed securely in a bead holder such as the holder shown in FIG. 3 of U.S. Patent No. 4,200,613. Then the bead together with the holder was inserted into the glass test tube. The tubes were shaken on a rotary shaker for 30 minutes. For tubes containing beads only, that is, without bead holders, the florescence of the solution can be read directly without removing the beads. For solutions in tubes containing beads secured in bead holders, however, removal of the holders together with the beads was required before the fluorescence was read.

The following Table I indicates the results obtained by using the aforementioned protocols for a number of samples having different amounts of the drug gentamicin.

TABLE I

| Concentration of Gentamicin in Serum | Fluorescence Units | |
|---|---|---|
| | Bead and Holder Removed from Tube | Bead Remaining in Tube |
| $\mu$g/ml | | |
| 0 | 394 | 91 |
| 2 | 714 | 152 |
| 5 | 1034 | 477 |
| 10 | 1328 | 742 |

The following reagents were prepared for use in the assays described in Examples 2 and 3:

| Assay Buffer: | 0.01 M phosphate buffer, pH 7.4 |
| | 0.15 M sodium chloride |
| | 0.1% sodium azide |
| | 0.1% Bovine serum albumin |
| Fluorescent Conjugate: | Fluorescent aminoglycoside conjugate (2.5 × $10^{-8}$ M) |
| Antibody Bead: | Polystyrene bead coated with purified antibody |

In addition, serum-based standard or sample solutions containing 0, 2, 5 and 10 micrograms of gentamicin or tobramycin per milliliter were prepared.

EXAMPLE 2

A quantity of 20 $\mu$l of the sample solution was drawn into a diluter and dispensed with 500 $\mu$l of fluorescent conjugate into a 12 ×75mm polystyrene test tube. A 20 $\mu$l aliquot of the thus diluted sample was further drawn from the polystyrene test tube and dispensed with 500 $\mu$l of the fluorescent conjugate into a 12 ×75mm glass test tube containing the antibody-coated bead, and further containing 700 $\mu$l of the assay buffer. The glass tube was then capped and placed in a Fisher hematology mixer and tumbled for thirty minutes. After withdrawal from the mixer, the florescence of the liquid phase above the bead was read in the fluorometer with the bead still remaining within the test tube.

The results of the assays, expressed in florescence units, are shown for each of the analyte samples in Table II.

TABLE II

| Gentamicin conc. | Fluorescence units |
|---|---|
| µg/ml | |
| 0 | 571 |
| 2 | 816 |
| 5 | 1145 |
| 10 | 1365 |
| Tobramycin conc. | Fluorescence Units |
| µg/ml | |
| 0 | 718 |
| 2 | 920 |
| 5 | 1197 |
| 10 | 1331 |

Under test conditions wherein the sample contains an unknown amount of aminoglycoside, the concentration of the analyte may be determined by comparing the fluorescence obtained with the unknown sample with a concentration-fluorescence plot obtained with the above results.

EXAMPLE 3

In an alternative example, 20 µl of the sample was diluted with 500 µl of assay buffer, and a 20 µl aliquot of the thus diluted sample was added to a 12 ×75 mm glass tube containing an antibody bead and 100 µl of assay buffer. Subsequently, 250 µl of the fluorescent conjugate was added. The glass tube was then shaken for 30 minutes on a variable rotator (Scientific Product Co.) at 220 r.p.m. Then 700 µl of the assay buffer was added to the tube and the fluorescence of the liquid above the bead was determined directly in the fluorometer without prior removal of the bead from the test tube.

The results are shown in Table III

TABLE III

| Gentamicin conc. | Fluorescence units |
|---|---|
| µg/ml | |
| 0 | 279 |
| 2 | 638 |
| 5 | 1031 |
| 10 | 1166 |
| Tobramycin conc. | Fluorescence units |
| µg/ml | |
| 0 | 727 |
| 2 | 1154 |
| 5 | 1325 |
| 10 | 1441 |

EXAMPLE 4

Assay Condition

The following reagents were prepared for use in the assay described in Example 4:

| PBS Buffer: | 0.01 M Phosphate Buffer, pH 7.4 |
|---|---|
| | 0.15 M Sodium Chloride |
| | 0.1% Sodium Azide |
| Fluorescent Conjugate: | Fluorescent Aminoglycoside Conjugate ($2.5 \times 10^{-8}$ M) |
| Antibody Bead: | Antibody Coated Polystyrene bead |

To carry out an assay, 20 µl of serum sample was mixed with 0.6 ml of PBS buffer in a 12 x 75mm glass test tube. The antibody bead was then added to the tube, which was subsequently put on a rack on top of a rotator and shaken for 1 hour. The bead was then removed and rinsed eight times with 3 ml of PBS buffer. After rinsing, the bead was placed in another 12 x 75mm glass tube containing 0.6 ml of fluorescent conjugate and shaken in a rotator. After 30 minutes, the tube was removed from the rotator and the bead was removed. Then 0.7 ml of PBS buffer was added to the tube and mixed. The fluorescence of the solution was measured in a fluorometer. The results are shown in Table IV.

TABLE IV

| Gentamicin Concentration in Sample | Fluorescence Units |
|---|---|
| µg/ml | |
| 0 | 88 |
| 2 | 737 |
| 5 | 843 |
| 10 | 1041 |

EXAMPLE 5

One can provide a tobramycin coated polystyrene bead and a fluorescein labeled anti-tobramycin serum. The tobramycin coated bead is mixed with the fluorescein labeled anti-tobramycin serum and the serum sample. The fluorescence of the liquid phase above the bead is determined by means of a fluorometer and the tobramycin concentration of the serum sample obtained by comparison with a plot of the fluorescence of a series of samples of known tobramycin concentration.

The foregoing description of the invention has been directed to a particular preferred embodiment for purposes of explanation and illustration. It will be apparent, however, to those skilled in the art that many modifications and changes in the methods and materials may be made without departure from the scope and spirit of the invention. For example, other antibodies, ligands and coating techniques may be used. Particular immunological systems described herein have been chosen for convenience and are not intended to be limiting. It is the applicants' intention in the following claims to cover all such equivalent modifications and variations as fall within the true spirit and scope of the invention.

What is claimed is:

1. A method for determining the concentration of an antigenic analyte ligand in a sample which comprises:
   mixing a solid phase supported antibody-fluorescently labeled antigenic analyte ligand complex with a liquid phase sample containing the antigenic analyte ligand to be determined, said liquid phase sample initially containing no fluorescently labeled antigenic analyte ligand, whereby the unlabeled antigenic analyte ligand in said liquid phase sample displaces a part of said fluorescently labeled antigenic analyte ligand from said solid phase supported antibody-fluorescently labeled antigenic analyte ligand complex into the liquid phase, resulting in
   (1) a solid phase containing:
      (a) solid phase supported antibody-fluorescently labeled antigenic analyte ligand complex, and
      (b) solid phase supported antibody-unlabeled antigenic analyte ligand complex, both complexed to said solid phase, and
   (2) a liquid phase containing:

(a) fluorescently labeled antigenic analyte ligand displaced from said solid phase supported antibody-fluorescently labeled antigenic analyte ligand complex, and (b) a reduced concentration of unlabeled antigenic analyte ligand;

measuring the fluorescence of the resulting liquid phase without measuring the fluorescence of the resulting solid phase and without separating the resulting solid phase from the resulting liquid phase; and determining the concentration of the antigenic analyte ligand in the sample corresponding to the measured fluorescence of the resulting liquid phase.

2. A method according to claim 1 wherein said ligand is an aminoglycoside.

3. A method according to claim 1 wherein said ligand is gentamicin.

4. A method according to claim 1 wherein said ligand is tobramycin.

* * * * *

UNITED STATES PATENT AND TRADEMARK OFFICE
CERTIFICATE OF CORRECTION

PATENT NO. : 4,977,077

DATED : Dec. 11, 1990

INVENTOR(S) : Ngo and Wong

It is certified that error appears in the above-identified patent and that said Letters Patent is hereby corrected as shown below:

Col. 4, line 1, after "antibody" add ----- (the hyphen symbol);

Col. 7, line 21, delete "4.C" and insert --4°C.--

Col. 7, line 34, center the title.

Signed and Sealed this

Twenty-sixth Day of May, 1992

Attest:

DOUGLAS B. COMER

Attesting Officer

Acting Commissioner of Patents and Trademarks